(12) United States Patent
Saclier et al.

(10) Patent No.: US 7,661,534 B2
(45) Date of Patent: Feb. 16, 2010

(54) CONTAINMENT FOR SUPPLYING INDIVIDUAL POUCHES

(75) Inventors: Christian Saclier, Ambilly (FR); Marco Ackermann, Conches (CH); Richard Miles, London (GB); Matthew Grey, London (GB)

(73) Assignee: Novartis, AG (CH)

( * ) Notice: Subject to any disclaimer, the term of this patent is extended or adjusted under 35 U.S.C. 154(b) by 354 days.

(21) Appl. No.: 11/455,033

(22) Filed: Jun. 16, 2006

(65) Prior Publication Data

US 2007/0045148 A1 Mar. 1, 2007

(30) Foreign Application Priority Data

Jun. 17, 2005 (EP) .................................. 05013088
Mar. 24, 2006 (GB) .................................. 0605997.6

(51) Int. Cl.
B65D 83/04 (2006.01)
B65D 1/34 (2006.01)
B65D 21/00 (2006.01)

(52) U.S. Cl. ........................ 206/535; 206/499; 206/554

(58) Field of Classification Search ................. 206/535, 206/536, 537, 499, 425, 554, 555
See application file for complete search history.

(56) References Cited

U.S. PATENT DOCUMENTS

| | | | |
|---|---|---|---|
| 2,809,766 A | 10/1957 | Anderson | 220/55 |
| 2,920,759 A | 1/1960 | Carnes | 206/56 |
| 3,388,836 A | 6/1968 | Otto et al. | |
| 3,894,655 A | 7/1975 | Mattheis et al. | 220/283 |
| 4,048,051 A | 9/1977 | Gretz | 206/1.5 |
| 4,098,430 A | 7/1978 | Mattheis et al. | 220/339 |
| 4,219,116 A | 8/1980 | Borkan | 206/1.5 |
| 4,511,032 A | 4/1985 | Bush | 206/1.5 |
| 4,890,742 A | 1/1990 | Allison | 206/540 |
| 4,913,311 A | 4/1990 | Garcia | |
| 5,033,634 A | 7/1991 | Batchelor et al. | 220/281 |
| 5,050,752 A | 9/1991 | Zoltan et al. | 215/206 |
| 5,082,114 A | 1/1992 | Bunin | 206/539 |
| 5,267,668 A | 12/1993 | Jones | 220/326 |
| 5,346,069 A | 9/1994 | Intini | 206/531 |

(Continued)

FOREIGN PATENT DOCUMENTS

EP 0 027 589 A1 4/1981

(Continued)

*Primary Examiner*—Ehud Gartenberg
*Assistant Examiner*—Jose S Stephens, III
(74) *Attorney, Agent, or Firm*—Frank A. Smith

(57) ABSTRACT

A containment (3;3a;3b;3c) comprises an outer box (2;2a;2b;3c) defining an inner space where a stack of individual pouches (1;1a) is arranged. The individual pouches each have a pocket (10) containing a product, e.g. a thin-film strip (FS), and are designed to be individually removed from the stack. The outer box (2;2a;2b;2c) comprises a closure (26;26a;26b;26c) for preventing/allowing access to the individual pouches (1;1a) and further comprises means (20;20a;20b;20c) for interacting with the pouches (1;1a) in a manner such as to allow access to the pocket (10) upon removing the pouch from the stack. The means (20;20a;20b;20c) for interacting with the pouches are arranged such that upon removing a pouch (1;1a) from the stack the pouch is opened along an essential part of its longitudinal extension and is completely removed from the outer box (2;2a;2b;2c) with no residual part of the pouch (1;1a) remaining in the outer box.

17 Claims, 10 Drawing Sheets

U.S. PATENT DOCUMENTS

| | | | |
|---|---|---|---|
| 5,499,740 A | 3/1996 | Huck et al. | |
| 5,575,399 A | 11/1996 | Intini | 220/326 |
| 5,613,779 A | 3/1997 | Niwa | |
| 5,718,347 A | 2/1998 | Walker et al. | 215/209 |
| 5,738,211 A | 4/1998 | Ichino et al. | |
| 5,740,938 A | 4/1998 | Hofmann et al. | 220/324 |
| 5,752,615 A | 5/1998 | Hofmann et al. | 220/324 |
| 5,860,550 A * | 1/1999 | Miller et al. | 220/4.23 |
| 5,931,304 A | 8/1999 | Hammond et al. | |
| 6,021,901 A | 2/2000 | Wolfe | 206/531 |
| 6,244,467 B1 * | 6/2001 | Lewit | 222/107 |
| 6,401,926 B1 | 6/2002 | Lo | 206/531 |
| 6,460,693 B1 | 10/2002 | Harrold | 206/1.5 |
| 6,478,156 B1 * | 11/2002 | Gebhardt | 206/554 |
| 6,679,381 B1 | 1/2004 | Bush | 206/531 |
| 6,702,462 B2 * | 3/2004 | Richardson | 383/200 |
| 6,708,826 B1 * | 3/2004 | Ginsberg et al. | 206/535 |
| 2004/0226853 A1 | 11/2004 | Intini | 206/536 |
| 2005/0103681 A1 * | 5/2005 | Aubry et al. | 206/767 |
| 2006/0006091 A1 | 1/2006 | Maietta | 206/539 |

FOREIGN PATENT DOCUMENTS

| | | |
|---|---|---|
| EP | 0 609 955 B1 | 4/1998 |
| EP | 1 574 451 A1 | 9/2005 |
| GB | 2 374 862 A | 10/2002 |
| JP | 05 072674 | 3/1993 |
| WO | WO 94/08872 | 4/1994 |
| WO | WO 96/22229 | 7/1996 |
| WO | WO 97/28058 | 8/1997 |
| WO | WO 03/094823 A1 | 11/2003 |
| WO | WO 2005/049438 A1 | 6/2005 |
| WO | WO 2005/068304 A2 | 7/2005 |

* cited by examiner

CONTAINMENT FOR SUPPLYING INDIVIDUAL POUCHES

The invention generally deals with the supply of individual pouches containing a product such as one or more thin-film strips, e.g. pharmaceutical film strips. More particular, the invention deals with a containment comprising an outer box in the inner space of which a stack of individual pouches is arranged. Further aspects of the invention are related to the outer box as well as to the individual pouches contained in the outer box.

Various products can be formulated in individual dosage units. In particular, personal care products can be formulated e.g. as tablets or capsules to be swallowed, as lozenges or strips of soluble film to be allowed to dissolve in the mouth, or as strips of bioadhesive film composition for treating wounds. Examples other than personal care products are also known, such as soluble peppermint strips to dissolve in the mouth. Sometimes it is important or desirable that each dose be segregated from the others—that is to say, the doses must not or should not all be held in the same bottle or vial. This might be the case, for example, if the formulation can be deleteriously affected by humidity (e.g. when the formulation is hygroscopic). Also, if the dosage form is such that the patient could easily and unknowingly take two dosage units at one time when only one single unit was prescribed, it is desirable to package each dose individually.

Containments coping with these requirements are already known in the art. One example for such a containment is described in U.S. Pat. No. 6,708,826 B1. The containment disclosed there comprises an outer box consisting of a bottom part and two lid parts hingedly attached to the bottom part. In the inner space defined by the bottom part and the two lid parts, a stack of individual pouches is arranged. The individual pouches each comprise a pouch portion and a tab portion. Each tab portion is provided with two holes each being penetrated by an upstanding post. The tab portions of the whole stack of individual pouches are held down by one of the two lids of the outer box. Between the tab portion and the pouch portion of each individual pouch there is a preset tear line allowing the pouch portion to be torn off of the tab portion. It is thus possible for a person to grasp the respective free end of a pouch and to tear it off of the tab portion. During tearing the pouch portion off of the tab portion, the pocket may be automatically opened along the tear line. However, since the tear line runs in the transverse direction of the pocket it may be difficult to access the product contained in the pocket because of the comparatively small dimensions of the opening created. For that reason, it is additionally suggested to manually tear the pouch portion along a further longitudinally running preset tear line in order to conveniently get access to the product contained in the pouch. Unfortunately, this requires an additional separate handling step which is inconvenient for the user. A further disadvantage is, that the tab portions of the individual pouches always remain in the outer box, so that these tab portions have to be disposed of separately once all pouch portions have been removed from the stack. Another disadvantage is, that—starting with the uppermost pouch—the more packages have been removed from the stack the more it gets difficult to grasp the lower ones of the pouches, since the remaining tab portions of the upper pouches are holding the lower pouches down.

It is therefore an object of the present invention to overcome this inconvenience and to avoid the above-mentioned disadvantages of the prior art packaging concept.

This object is achieved by a containment as it is characterized by the features of independent claim directed to a containment. Preferred embodiments of the containment are the subject of the respective dependent claims. As far as it concerns the pouch, this object is achieved by a pouch as it is characterized by the features of the independent claim directed to a pouch. Preferred embodiments of the pouch are the subject of the respective dependent claims. Finally, as far as the outer box is concerned, this object is achieved by a box as it is characterized by the features of the independent claim directed to a box. Preferred embodiments of the box are the subject of the respective dependent claims.

In particular, the containment according to the instant invention comprises an outer box defining an inner space where a stack of individual pouches is arranged. The individual pouches each have a pocket containing a product, e.g. one or more thin-film strips such as a pharmaceutical film strip. The individual pouches are designed to be individually removed from the stack. The outer box comprises a closure for preventing/allowing access to the individual pouches and further comprises means for interacting with the pouches in a manner such as to allow access to the pocket of an individual pouch upon removing the pouch from the stack. The means for interacting with the pouches are arranged such that upon removing a pouch from the stack the pouch is opened along an essential part of its longitudinal extension and is completely removed from the outer box with no residual part of the pouch remaining in the outer box.

Accordingly, it is possible to remove an entire pouch from the stack without any part of the individual pouch being retained in the outer box. As a consequence, it is no longer necessary to separately dispose of any rests of the pouches once all pouches have been removed from the box. Also, selective separation of the waste materials (e.g. polyethylene/ aluminum/polyethyleneterephthalate for the pouch; polypropylene for the outer box) of the components is possible, thus further improving waste management. Also, since the pouch is opened along an essential part of its longitudinal extension, the pocket containing the product—e.g. the pharmaceutical film strip—is opened to an extent that it conveniently allows access to the product. A further important advantage is, that since the uppermost individual pouch is always completely removed from the outer box with no tab portions remaining in the outer box, grasping of the individual uppermost pouch and removing it from the outer box is facilitated.

In a preferred embodiment of the containment according to the invention, the outer box comprises a bottom, two sidewalls, an optional end wall, a lid, and an open end allowing access to the pouches when the closure is open. The means for interacting with the pouches comprise an upstanding post arranged on the bottom of the outer box in a region close to the open end of the outer box. The upstanding post extends through a hole provided in an end region of each of the pouches. This embodiment is easy to manufacture and easy to handle as well.

The upstanding post may have—in a preferred embodiment—a pointed edge facing in the direction of the longitudinal extension of the pouches. This facilitates rupturing of the pouch during removal.

In a further preferred embodiment of the containment according to the instant invention, the closure is hingedly attached to the rest of the outer box. This allows to easily open and close the outer box in order to get access to the individual pouches contained in the outer box.

According to another embodiment of the containment, the closure is a piece which is manufactured separately from the outer box and which is pivotally attached to the rest of the outer box by means of a laterally arranged hinge. Alternatively, the closure may be a piece which is integrally formed with the rest of the outer box and which is attached to an edge at the open end of the box by a living hinge. Both options are comparatively easy to manufacture.

In a further preferred embodiment of the containment according to the invention, the closure as well as the rest of the outer box both comprise interengaging means allowing to retain the closure in a locked state so as to prevent access to the pouches and to release it for allowing access to the pouches. This improves safety of the containment against unintentional opening or unlocking.

Preferably, the closure as well as the rest of the outer box both comprise a plurality of spatially separated interengaging means being arranged such that the closure is releasable from the locked state only when all of the plurality of interengaging means are operated. This further improves safety of the containment against unintentional opening or unlocking, and in particular provides good child resistance.

For example, the plurality of interengaging means can be arranged such that the closure is releasable from the locked state when all of the plurality of interengaging means are operated simultaneously. This embodiment is an easy to manufacture example of a containment providing particularly good child resistance.

In particular, the above described embodiments of interengaging means comprise a releasable snap-fit.

In a still further preferred embodiment of the containment according to the invention, the lid as well as the closure both comprise additional interengaging means allowing to retain the closure in the locked state to prevent access and to release it for allowing access to the inner space of the box. Such interengaging means additionally improve safety of the containment against unintentional opening or unlocking, and in particular provide a superior child resistance.

Preferably, the lid has receiving means for receiving a finger of a user to apply pressure for releasing the closure from the lid. Thus, it can be assured that a user pushes the lid at the right position allowing to easily release the closure from the locked state.

An edge of the lid being arranged adjacent to an edge of the closure when the box is in the locked state, preferably projects above the edge of the closure. This ensures a proper dosing of the box even if the box has been opened and dosed for a plenty of times. In particular, it prevents that a gap between the edges of the lid and of the closure is generated by repeatedly using the box. Such a gap could result in an unintentional release of the closure from the lid and could deteriorate child resistance.

In still a further preferred embodiment of the containment according to the instant invention, the lid of the outer box is hingedly attached to the rest of the outer box. This allows to open the lid of the box in a simple manner and to "load" the outer box by inserting a stack of individual pouches. The outer box can then easily be closed again and is ready for use. In particular, the lid may be integrally formed with the rest of the box and is attached to an edge of the end wall via a living hinge. This is an embodiment which facilitates manufacture.

In still a further embodiment of the containment according to the instant invention, both the outer box at its open end as well as the pouches at their respective ends are shaped such, that the pouches are exposed at that side where the upstanding post is arranged. Thus, the user has access to and grasps the pouch on that side where the post is arranged and pulls it out of the outer box which facilitates removal of the individual pouches, since the user grasps and pulls the pouch at a location where the minimal required force must be applied in order to remove the pouch from the box while opening it at the same time (by interaction of the post with the pouch).

In order to indicate to the user that he/she is to pull the pouch in order to remove it from the outer box, in a further preferred embodiment of the containment according to the invention the individual pouch has a marking on its upper side indicating the direction the pouch is to be pulled out of the outer box (e.g. an arrow).

As far as the individual pouch is concerned, the pouch according to the instant invention may contain a product, e.g. one or more thin-film strips such as a pharmaceutical film strip. The pouch comprises an upper sheet and a lower sheet connected to each other so as to form a pocket for accommodating the product. Furthermore, the pouch comprises a hole located outside of the pocket and close to a longitudinal end of the pouch. The hole is adapted for accommodating a means for interacting with the pouch such that upon pulling the pouch at its longitudinal end the package ruptures along an essential part of its longitudinal extension and through its oppositely arranged longitudinal end. As mentioned above, the pouch allows to conveniently access the product contained in the pocket, since upon interacting with the respective interacting means (such as e.g. a post) the pouch ruptures along an essential part of its longitudinal extension. Also, no parts of the pouch are remaining in an outer box but rather the entire pouch is completely removed from the outer box.

In order to facilitate rupturing, a preferred embodiment of the pouch according to the invention further comprises a preset rupturing line extending from the hole in the longitudinal direction of the pouch and causing the pouch to rupture along the preset rupturing line.

In a further particular embodiment, the hole is an oblong hole with one of its longitudinal ends being arranged directly adjacent to the preset rupturing line, so that the user may pull the pouch so as to cause the interacting means (e.g. post) to engage the pouch at the end of the oblong hole and to cause the pouch to start rupturing. To further facilitate rupturing, the hole, e.g. the oblong hole, may be provided at its end located adjacent to the present rupturing line with a slit extending in a direction towards the preset rupturing line.

In a further embodiment of the pouch, the hole, e.g. the oblong hole, may be provided with an additional slit extending in a direction transverse to the direction of the preset rupturing line, thus allowing to tear the package along a transversely running line, should this turn out to be desirable.

The preset rupturing line may be manufactured by scoring, e.g. by laser scoring, which is a technology that is well-established in this field.

In order to prevent the product contained in the pocket of the pouch, such as the thin-film strip, from being damaged upon causing the pouch to rupture, a further embodiment of the pouch according to the invention may comprise additional connection areas along the rupturing line where (that is to say at which connection areas) the upper and lower sheet of the pouch are connected (e.g. sealed). This makes sure, that the product such as the thin-film strip is always located in the pocket a distance away from the preset rupturing line, so that it cannot be damaged during rupturing of the pouch.

As far as the box is concerned, the box according to the instant invention defines an inner space for accommodating a stack of individual pouches as described hereinbefore. The box comprises a bottom, two side-walls, an optional end wall, a lid, and an open end allowing access to the inner space of the box when the closure is open. Further, the box comprises an upstanding post arranged on the bottom of the box in a region close to the open end of the box. The post is arranged for extending through the hole of the respective pouch, so that upon pulling the longitudinal end of the pouch out of the box the post causes the pouch to rupture in the longitudinal direction of the pouch thus removing the individual pouch from the stack and allowing access to the pocket of the pouch. The advantages of such a box have already been described above with respect to the containment and the pouches, they are therefore not reiterated here.

In a preferred embodiment of the box according to the instant invention, the upstanding post has a pointed edge facing in the direction opposite to the open end of the box. This facilitates rupturing of the pouches, as is already described further above.

According to a further embodiment of the box according to the invention, the closure is hingedly attached to the rest of the box. One way to achieve this is to use a closure which is a piece that is manufactured separately from the box and that is pivotally attached to the rest of the box by means of a laterally arranged hinge. Another way to achieve this is to use a closure, which is a piece integrally formed with the rest of the box and is attached to an edge of the open end by a living hinge.

In a further embodiment of the box according to the instant invention, the closure as well as the rest of the box, both comprise interengaging means allowing to retain the closure in a locked state to prevent access and to release it for allowing access to the inner space of the box. This is a technically simple and on the other hand reliable way to avoid unintentional opening of the box.

Preferably, the closure as well as the rest of the box both comprise a plurality of spatially separated interengaging means being arranged such that the closure is releasable from the locked state only when all of the plurality of interengaging means are operated. This further improves safety of the containment against unintentional opening or unlocking, and in particular provides good child resistance.

For example, the plurality of interengaging means are arranged such that the closure is releasable from the locked state when all of the plurality of interengaging means are operated simultaneously. This embodiment is an easy to manufacture example of a containment providing particularly good child resistance.

In particular, the above described embodiments of interengaging means comprise a releasable snap-fit.

In a still further preferred embodiment of the box according to the invention, the lid as well as the closure both comprise additional interengaging means allowing to retain the closure in the locked state to prevent access and to release it for allowing access to the inner space of the box. Such interengaging means additionally improve safety of the containment against unintentional opening or unlocking, and in particular provide a superior child resistance.

Preferably, the lid has receiving means for receiving a finger of a user to apply pressure for releasing the closure from the lid. Thus, it can be assured that a user pushes the lid at the right position allowing to easily release the closure from the locked state.

An edge of the lid being arranged adjacent to an edge of the closure when the box is in the locked state, preferably projects above the edge of the closure. This ensures a proper closing of the box even if the box has been opened and closed for a plenty of times. In particular, it prevents that a gap between the edges of the lid and of the closure is generated by repeatedly using the box. Such gap could result in an unintentional release of the closure from the lid and could deteriorate child resistance.

As already discussed above, the lid of the box may be hingedly attached to the rest of the box, thus facilitating "loading" of the box by inserting a stack of pouches. The lid may be integrally formed with the rest of the box and is attached to an edge of the end wall via a living hinge.

Other advantageous embodiments become apparent from the following detailed description of embodiments of the containment, the pouch and the box according to the instant invention with the aid of the drawings, in which.

Figure 4:
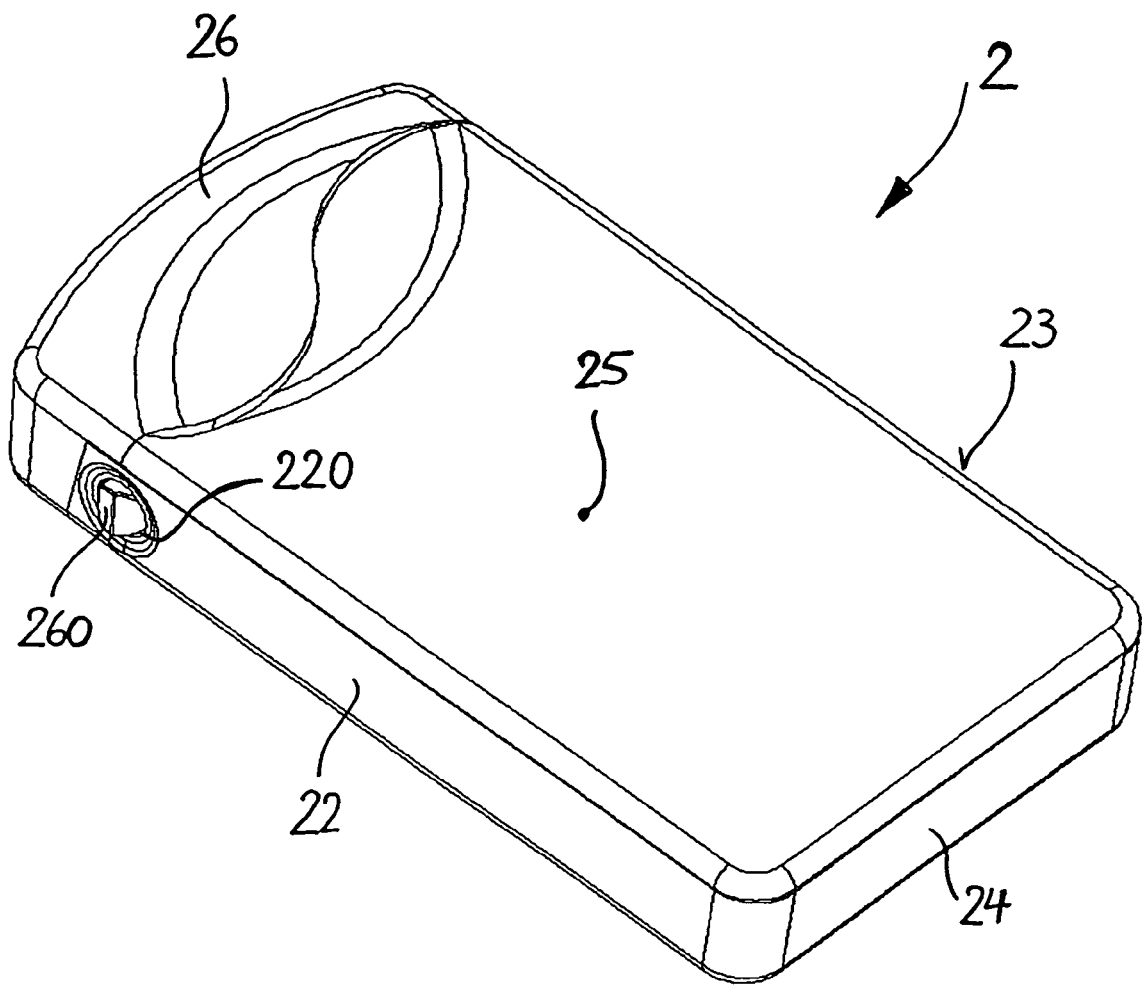
Figure 5:
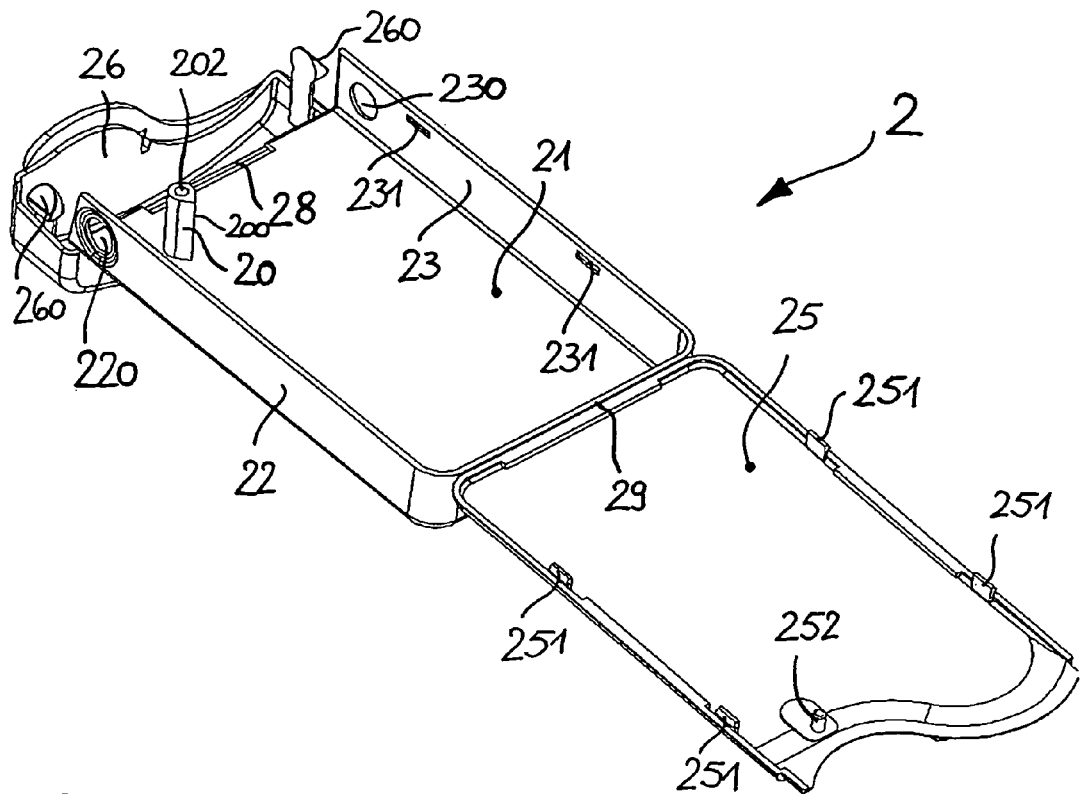
Figure 6:
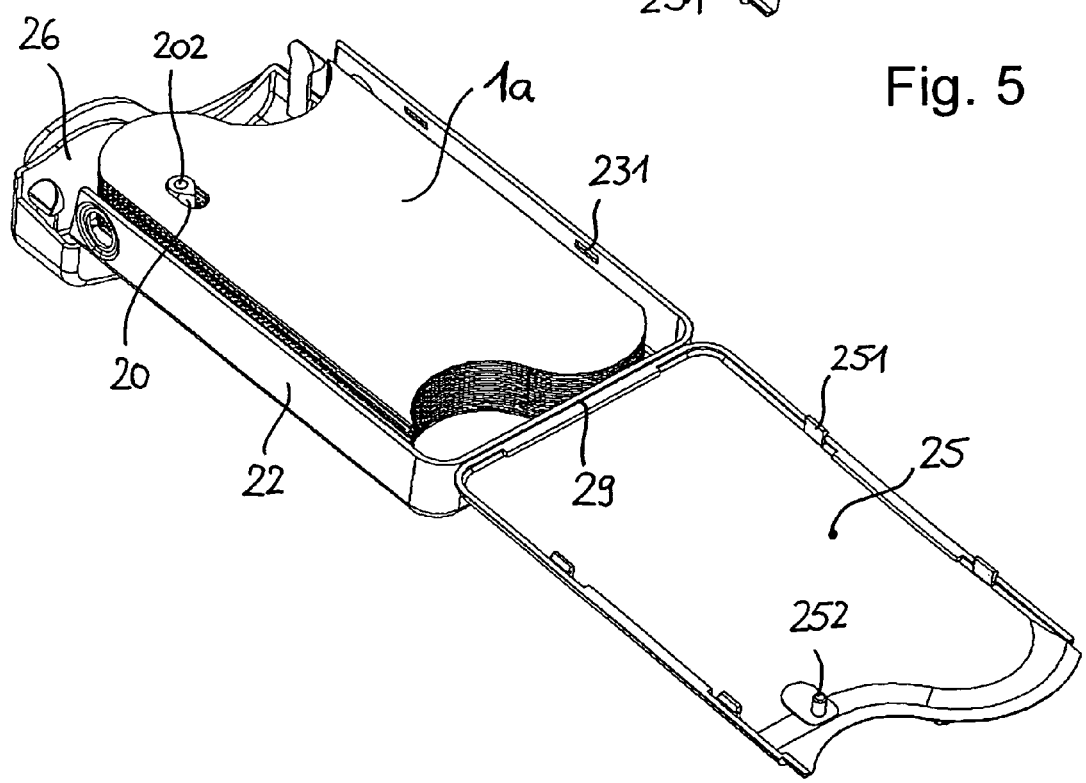
Figure 7:
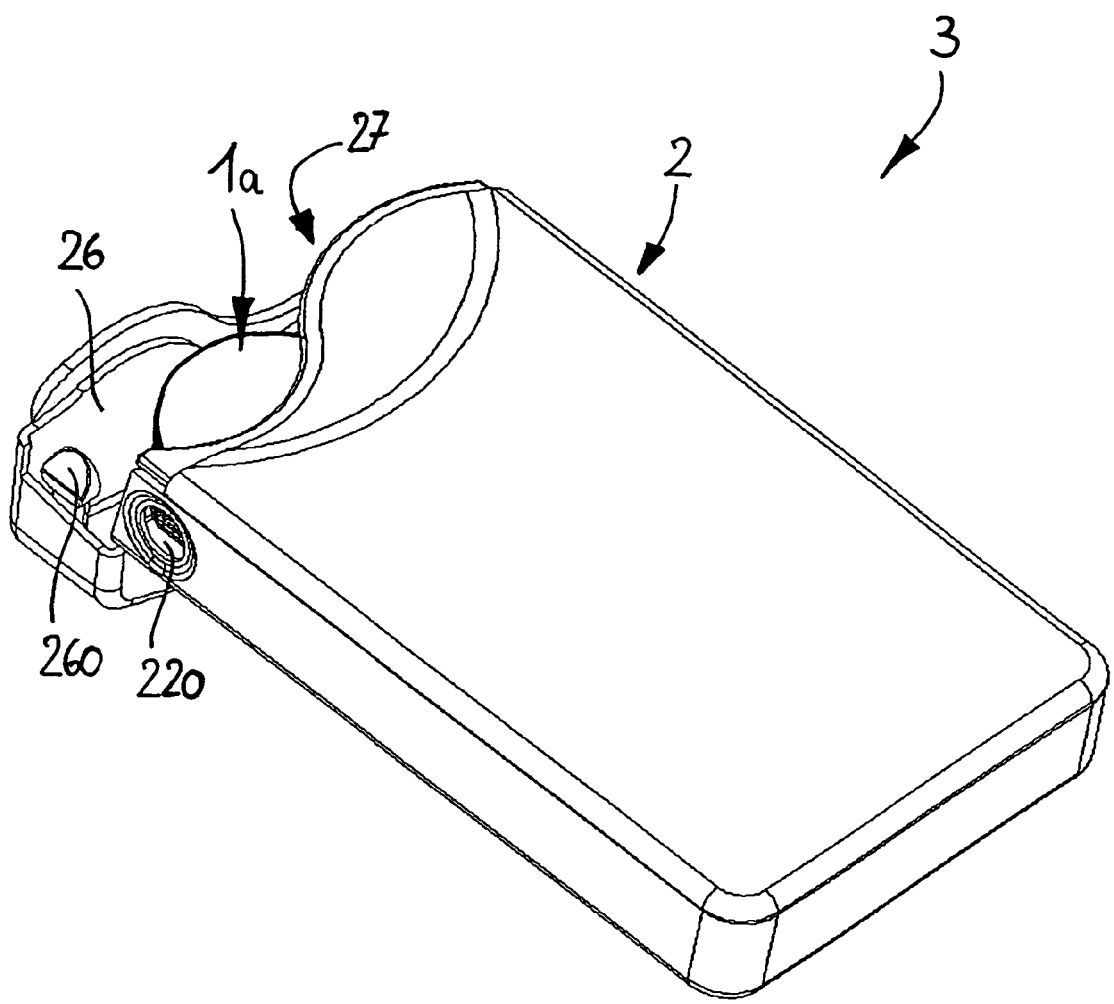
Figure 8:
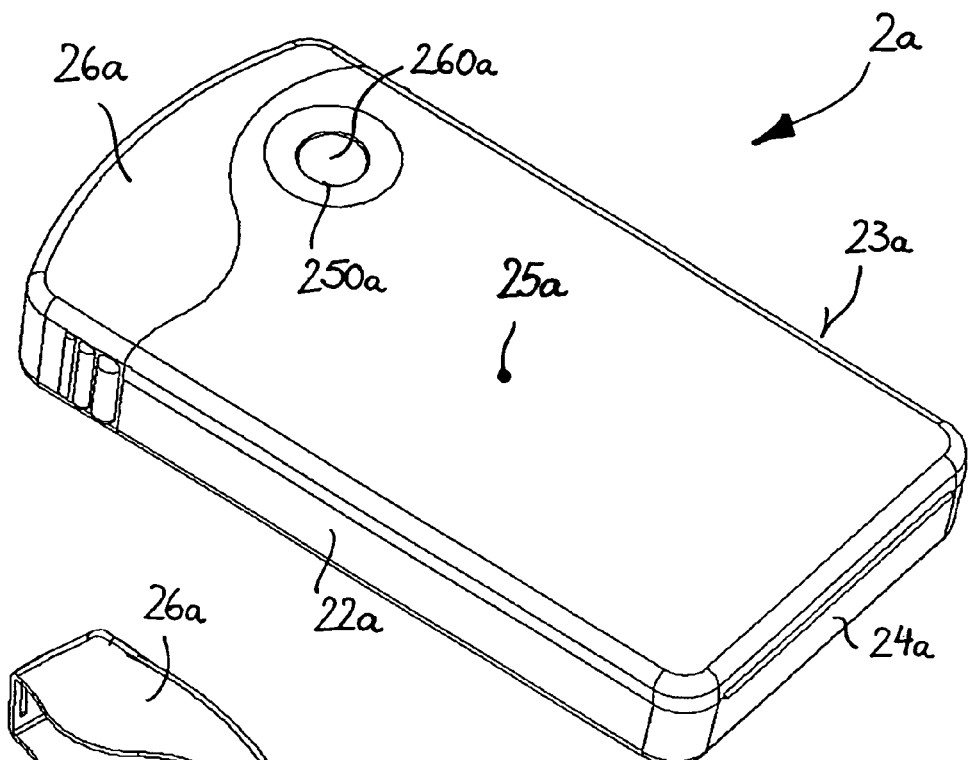
Figure 9:
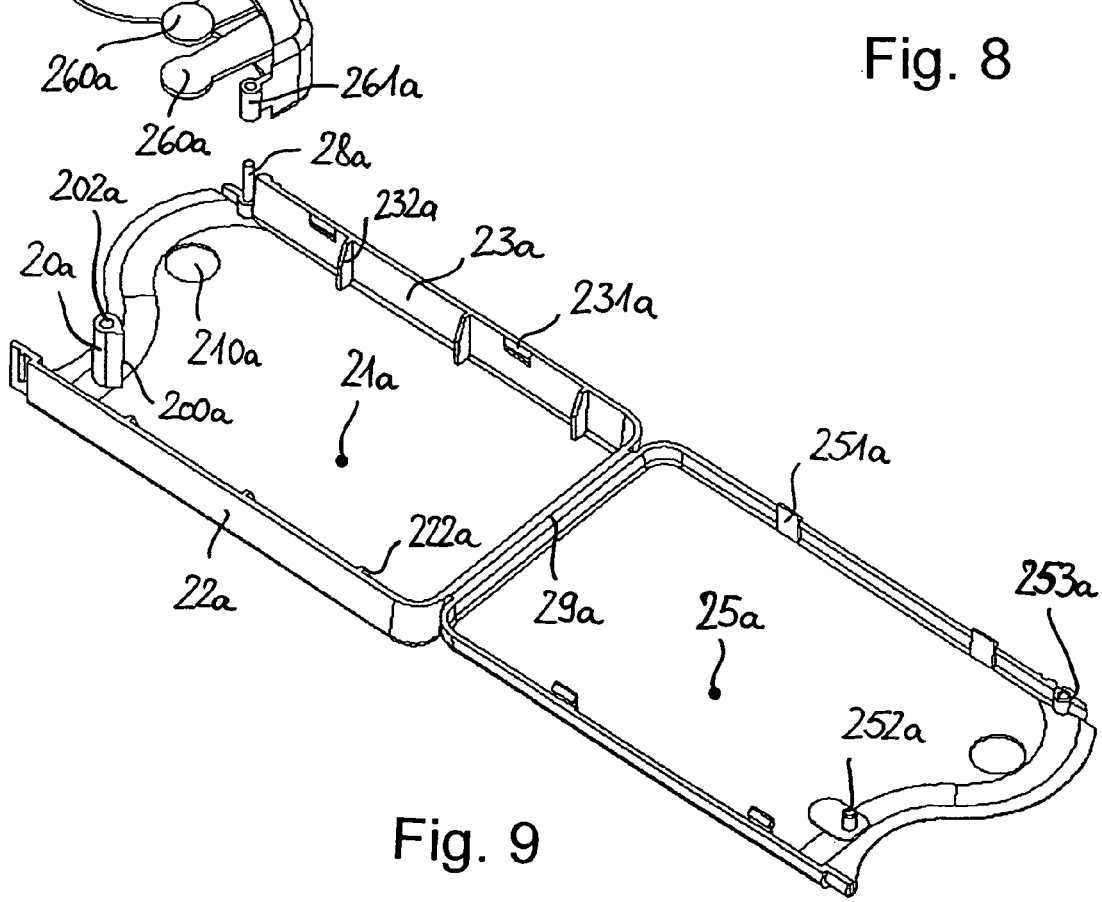
Figures 10, 11:
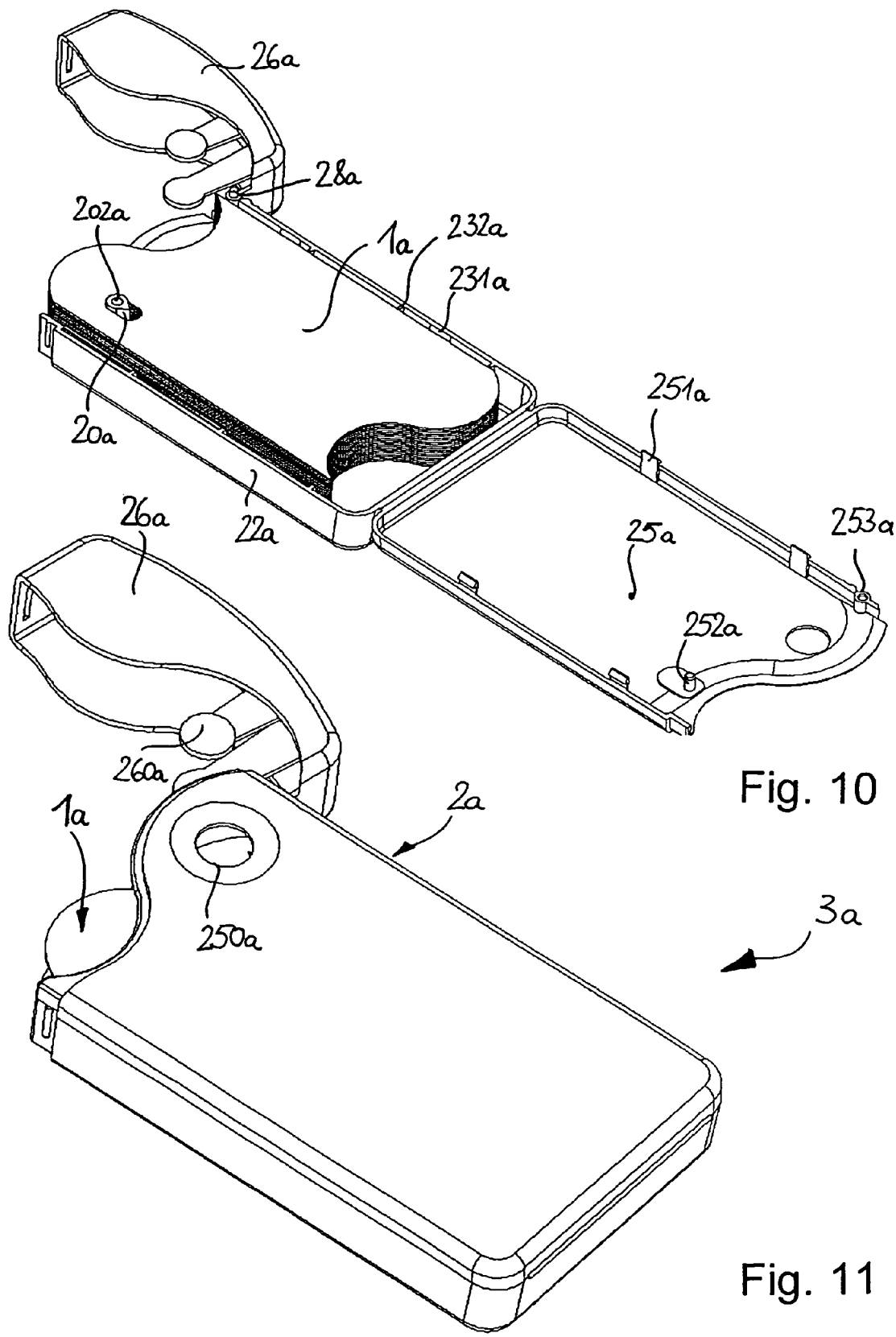
Figure 12:
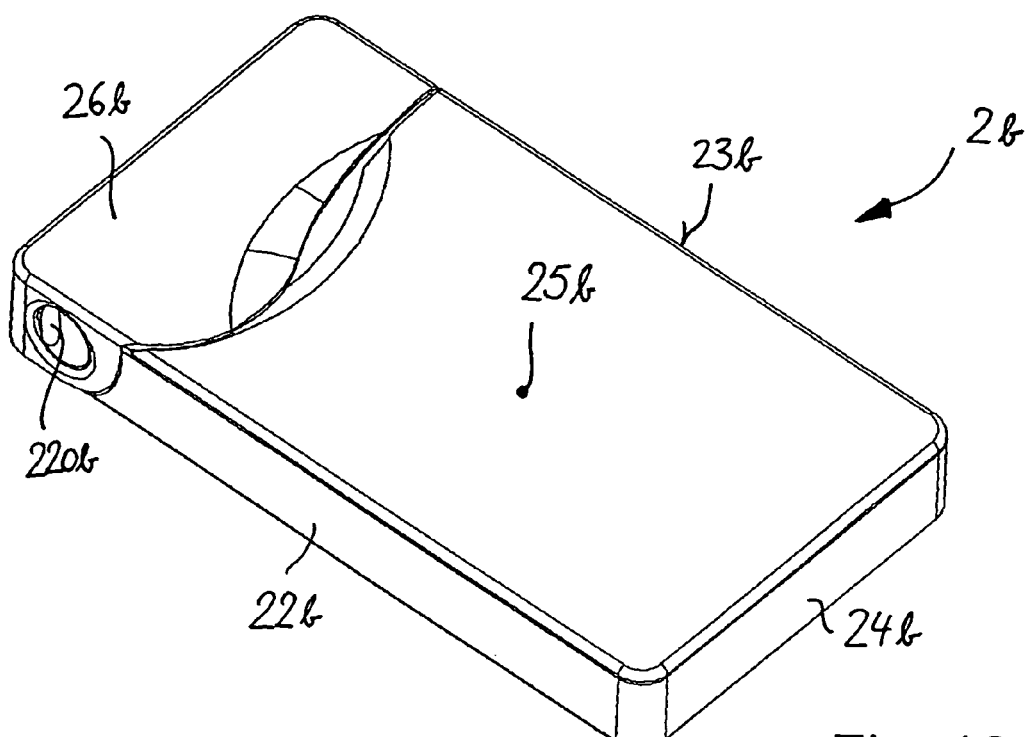
Figure 13:
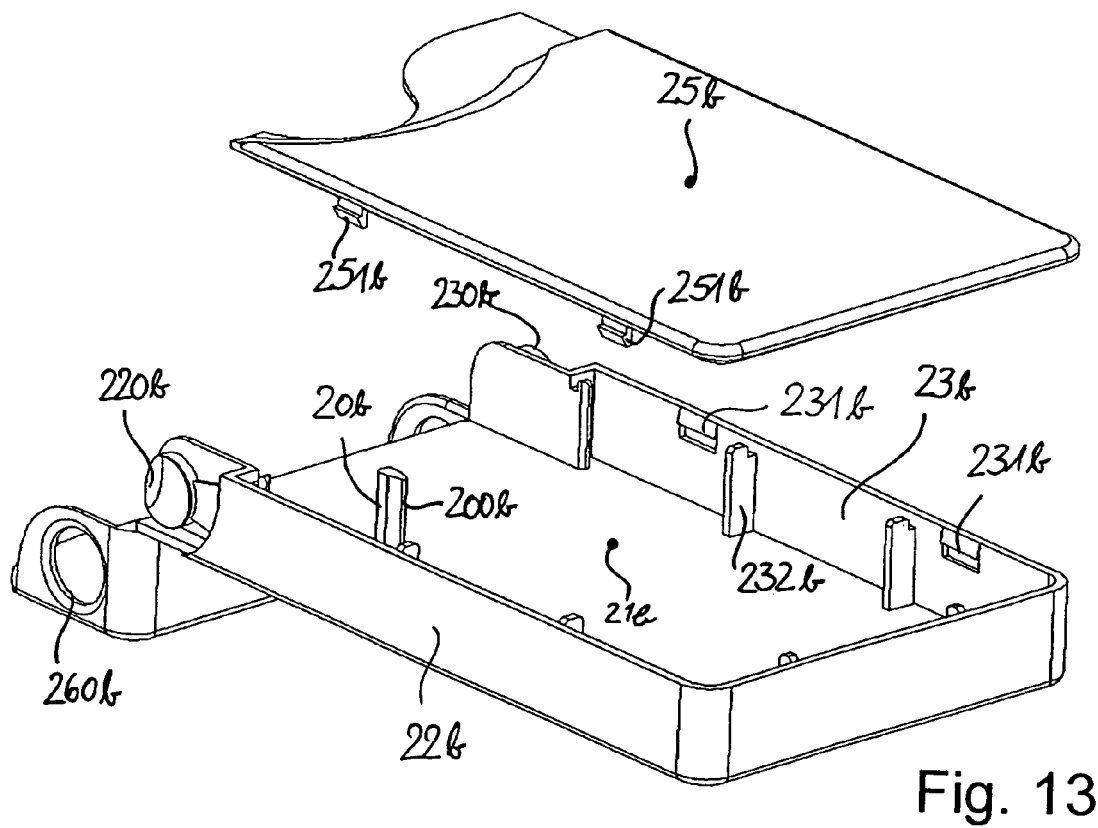
Figure 14:
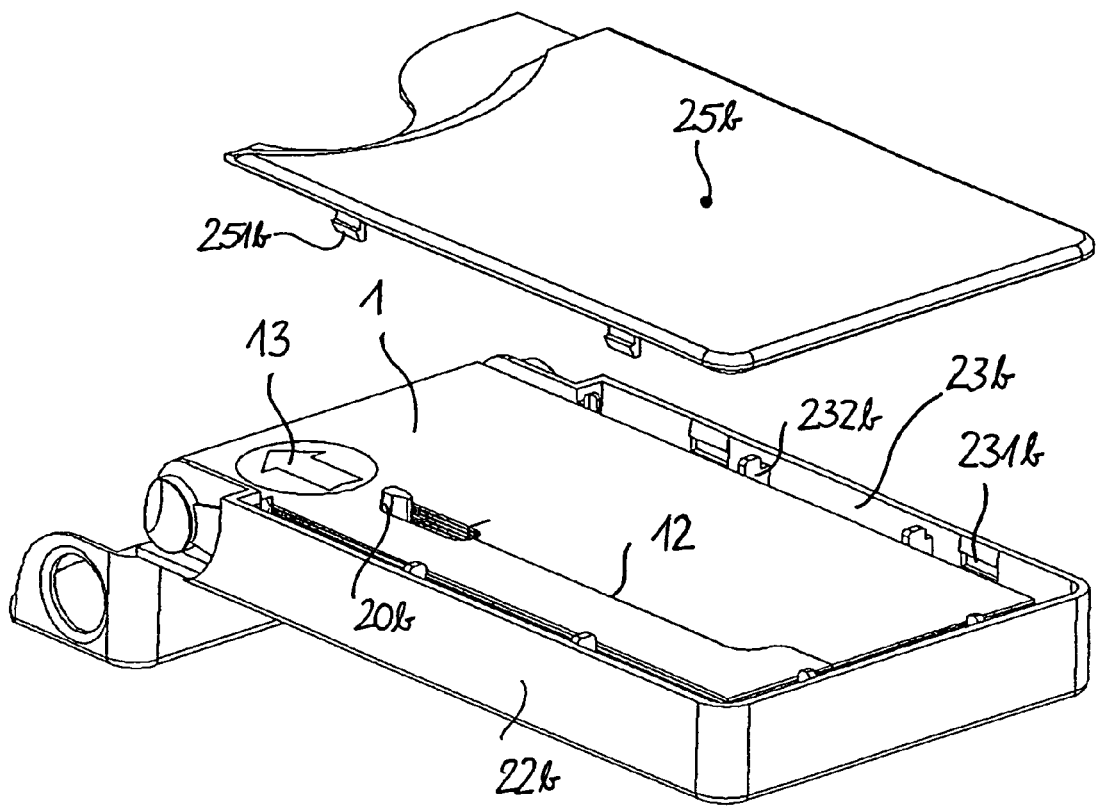
Figure 15:
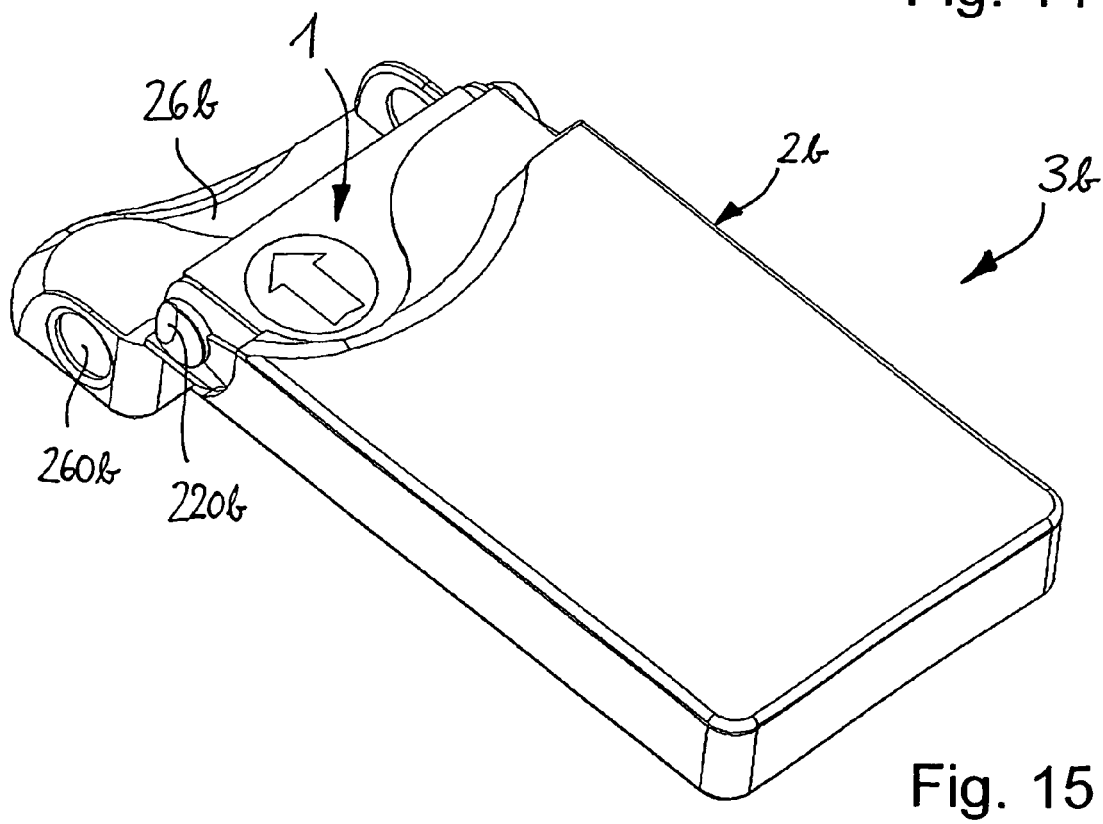

FIG. 4 shows a first embodiment of the box according to the instant invention in a closed state FIG. 5 shows the box according to FIG. 4 in a completely opened state FIG. 6 shows a first embodiment of the containment according to the instant invention in a completely opened state, the containment comprising the box of FIG. 4 as an outer box and a stack of pouches arranged in the outer box FIG. 7 shows the containment of FIG. 6 containing the pouches, in a state where only the closure is open FIG. 8 shows a second embodiment of the box according to the instant invention in a closed state FIG. 9 shows the box according to FIG. 8 in a completely opened state, with the separate closure being disassembled FIG. 10 shows a second embodiment of the containment according to the instant invention in a completely opened state, the containment comprising the box of FIG. 8 as an outer box and a stack of pouches arranged in the outer box FIG. 11 shows the containment of FIG. 10 containing the pouches, in a state where only the closure is open FIG. 12 shows a third embodiment of the box according to the instant invention FIG. 13 shows the box according to FIG. 12 in a completely opened state, with the separate lid being disassembled FIG. 14 shows a third embodiment of the containment according to the instant invention, comprising a box according to FIG. 12 as an outer box and a stack of pouches arranged in the outer box, and FIG. 15 shows the containment of FIG. 14 containing the pouches, in a state where only the closure is open.

Figure 16:
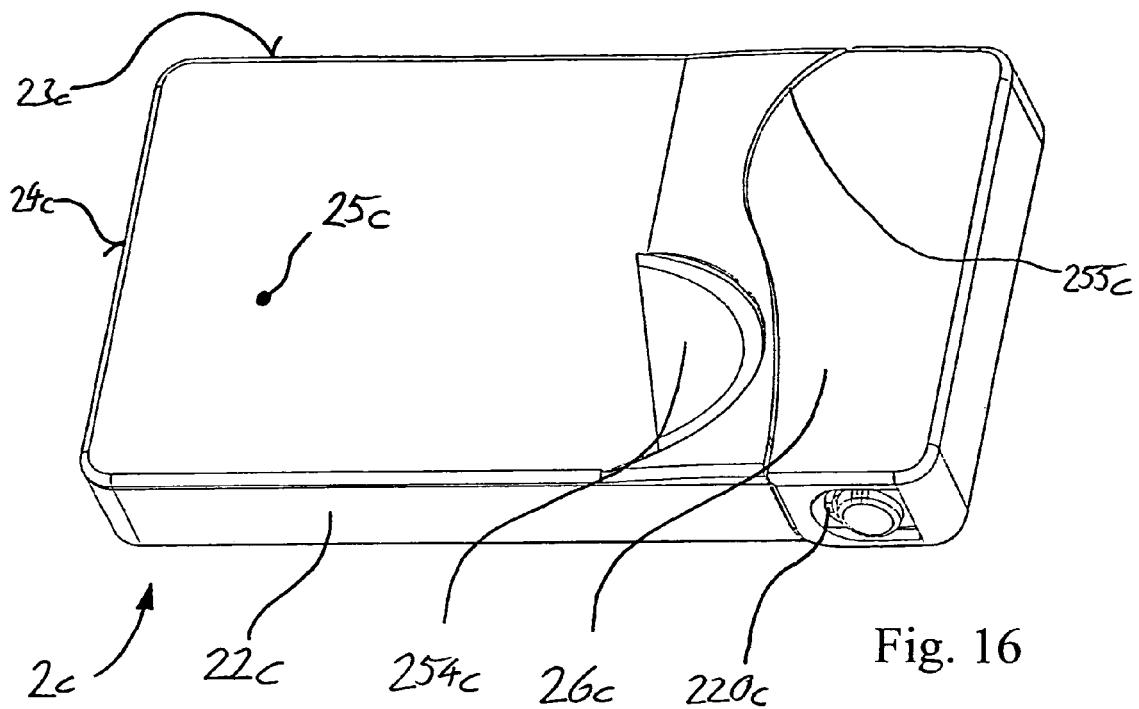

FIG. 16 shows a fourth embodiment of the box according to the instant invention

Figure 17:
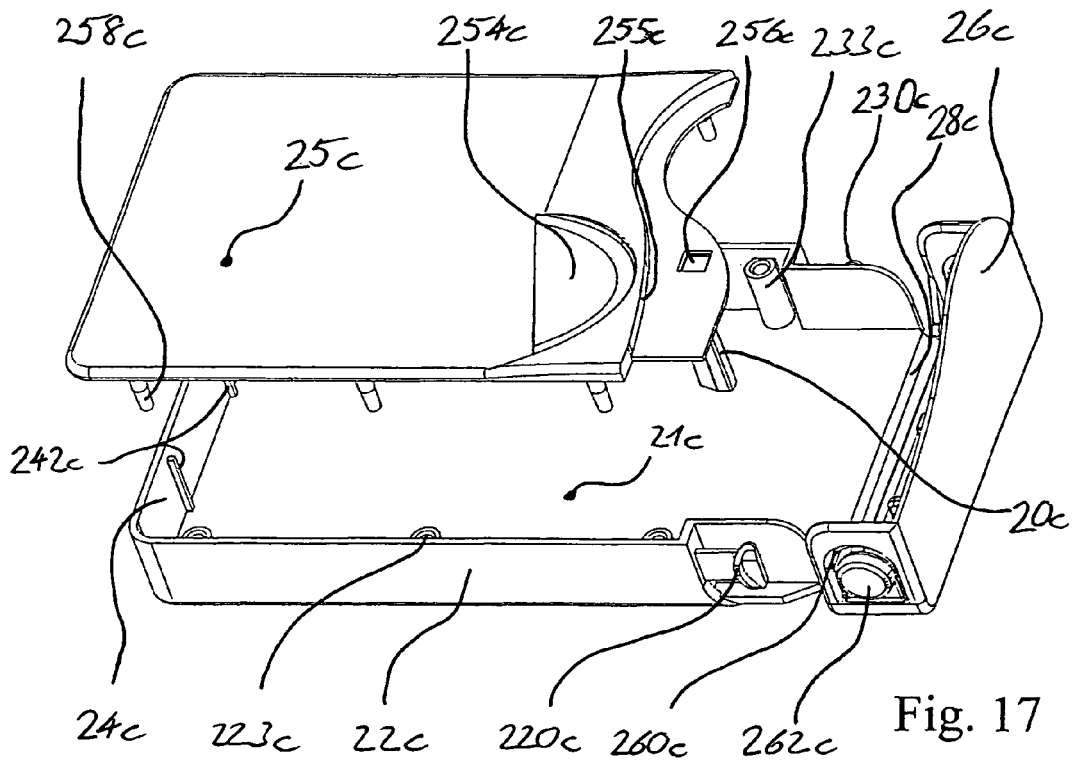
Figure 18:
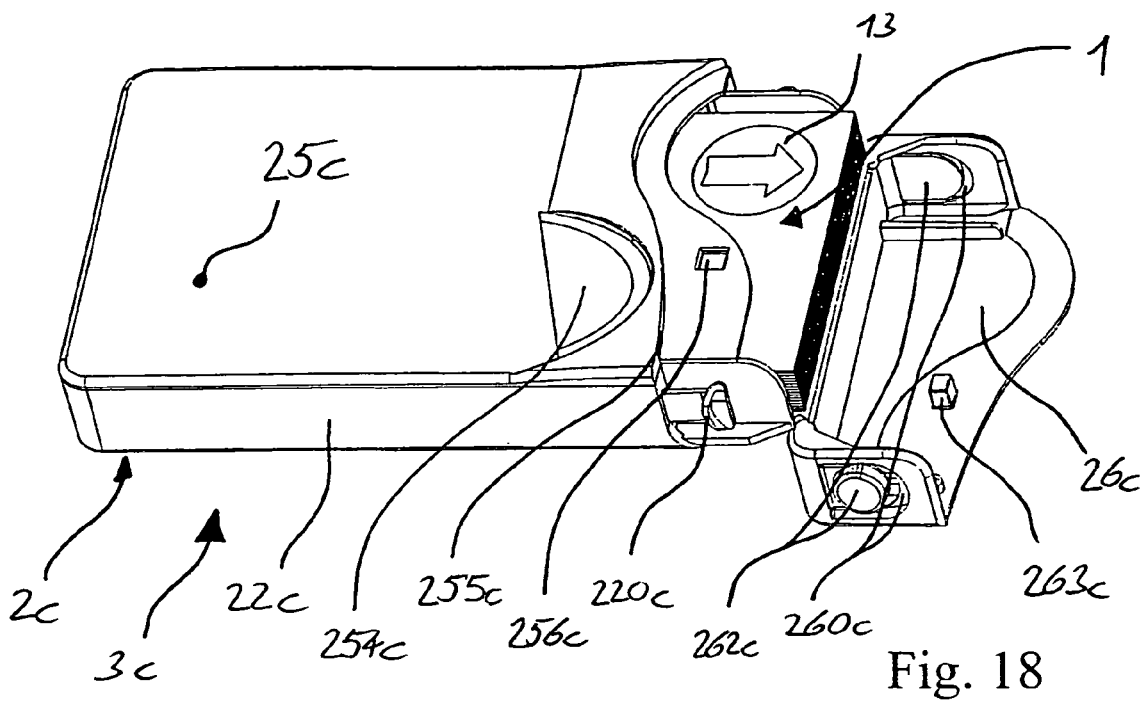
Figure 19:
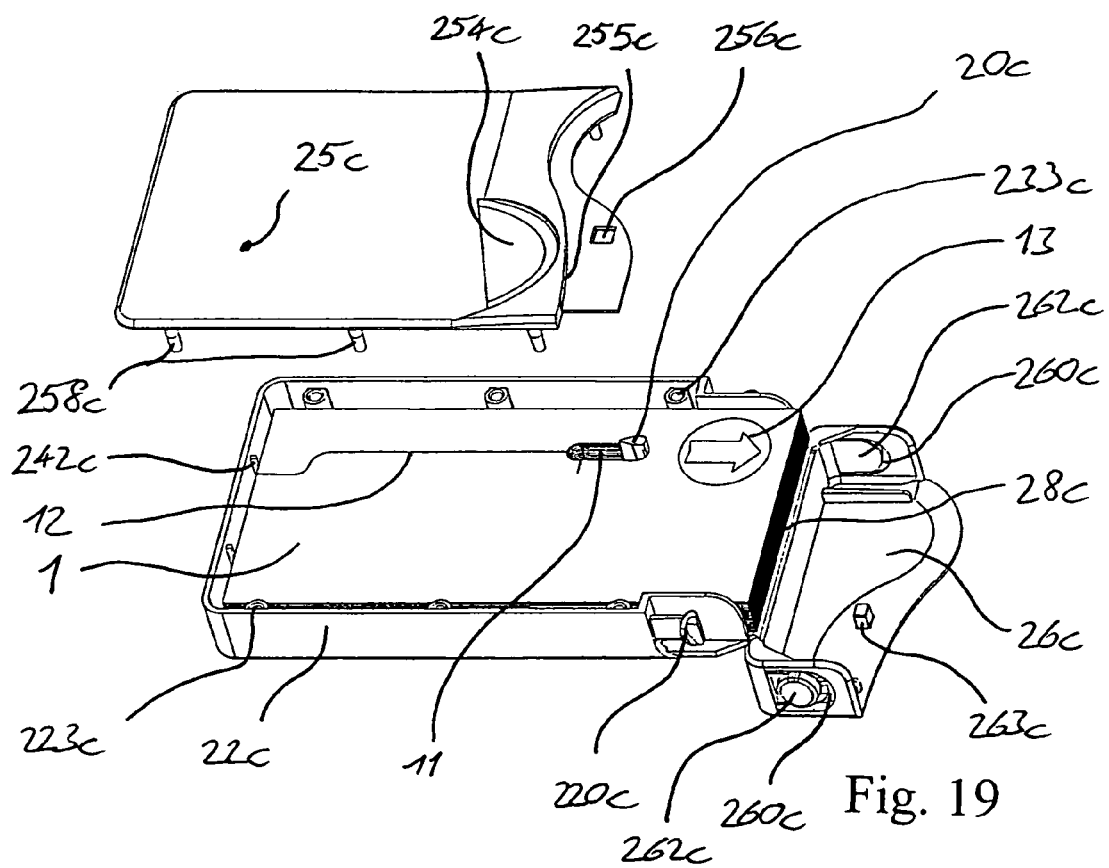

FIG. 17 shows the box according to FIG. 16 in a completely opened state, with the separate lid being disassembled FIG. 18 shows a fourth embodiment of the containment according to the instant invention, comprising a box according to FIG. 16 as an outer box and a stack of pouches arranged in the outer box, and FIG. 19 shows the containment of FIG. 18 containing the pouches, in a state where the closure open and the lid is disassembled.

Figure 1:
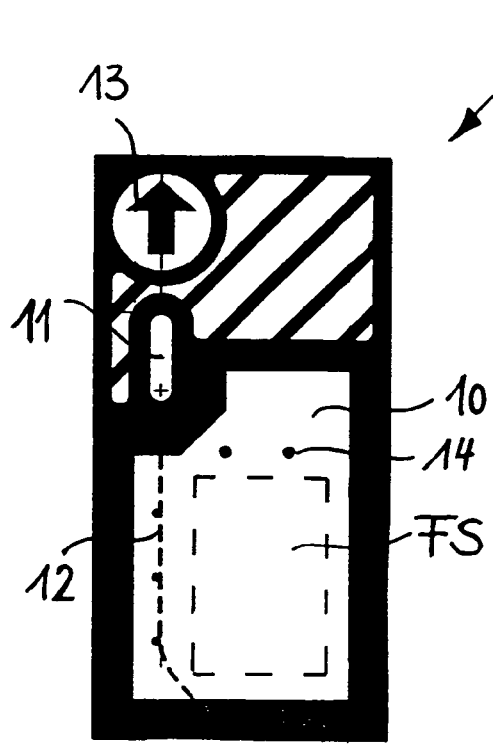
FIG. 1 shows an embodiment of a pouch according to the instant invention
Figure 2:
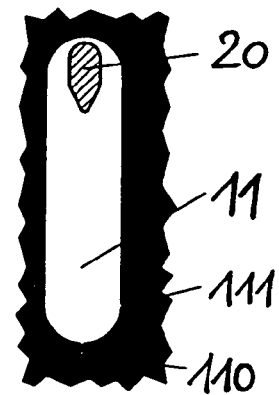
FIG. 2 shows in an enlarged view the oblong hole of the pouch shown in FIG. 1
Figure 3:
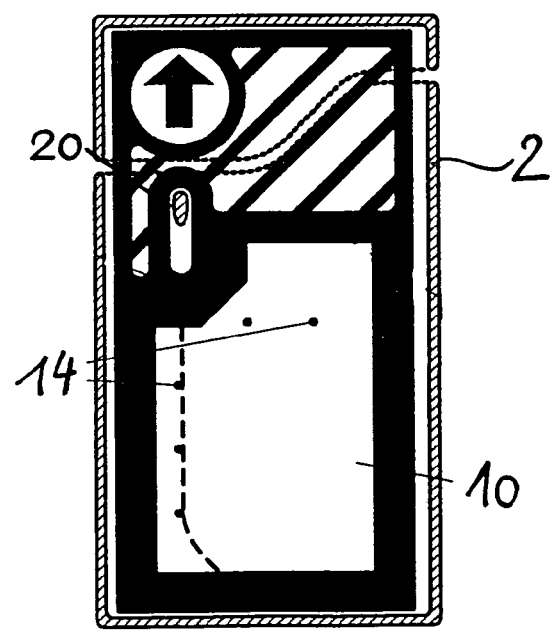
FIG. 3 shows the pouch according to FIG. 1 arranged within an outer box

FIG. 1 shows an embodiment of the pouch 1, which comprises essentially an upper sheet and a lower sheet which are connected to each other, e.g. by heat sealing. The sealed areas of the pouch are shown in black in FIG. 1 and define a pocket 10, in which a product such as a water-soluble pharmaceutical thin-film strip FS can be contained. As is shown in FIG. 1, pouch 1 comprises a hole, e.g. an oblong hole 11, through which a post 20 of an outer box 2 (see FIG. 3) extends. The oblong hole 11 may also have a shape other than the shape shown in FIG. 1, e.g. it may be rectangular, etc. It allows the pouch to be grasped in a simple manner and to be pulled out of the box a short distance before the pouch starts to rupture. The oblong hole 11 is shown in enlarged view in FIG. 2, from which it can be seen that at the longitudinal end of oblong hole 11, next to pocket 10, there is a slit 110 extending in the longitudinal direction, while there is also a slit 111 extending transverse thereto. As can be seen from FIG. 1, a preset rupturing line 12 is provided which can be manufactured by laser scoring, for example. Also, at the upper end of pouch 1, an arrow 13 is provided on the surface of pouch 1 indicating to the user that he/she has to pull pouch 1 out of outer box 2. During pulling pouch 1 in the direction of arrow 13, pouch 1 ruptures along preset rupturing line 12. Slit 110 arranged at the longitudinal end of oblong hole 11 allows to facilitate the start of the rupturing of pouch 1. As can be seen in FIG. 1, additional connection areas 14 may be provided along preset rupturing line 12 in order to prevent that the products contained in pocket 10, e.g. the thin-film strips FS, be damaged when the pouch ruptures, since the connection areas make sure that the products, e.g. thin-film strips FS, be located in pocket 10 a distance away from preset rupturing line 12.

FIG. 4 shows a first embodiment of the box 2 according to the instant invention, which box 2 serves as an outer box of a containment for a stack of pouches 1 as will be described in more detail below. Box 2 comprises a bottom 21 (see FIG. 5), two side-walls 22 and 23, an end wall 24 (which is not generally mandatory, but is present in the described embodiment), a lid 25 and a closure 26. When the closure 26 is open (see FIG. 7), an open end 27 is defined, through which the user can get access to the inner space of the box where the pouches 1a (the undulating-shaped pouches are referenced to as "1a", although they are very similar to rectangular-shaped pouches 1) are arranged.

Turning back to FIG. 4, box 2 is in the locked state. In order to retain box 2 in the locked state, means for interengaging are provided at closure 26 and at side-walls 22,23 as well. These interengaging means comprise two cams 260 resiliently attached to closure 26, as well as two holes 220 and 230 in the respective side-walls 22 and 23. Closure 26 is integrally formed with the box and is attached to an edge of bottom 21 at the open end 27 of box 2 by a living hinge 28. An upstanding post 20 having a pointed edge 200 extends from bottom 21. At the end wall 24, lid 25 is attached by means of a further living hinge 29.

In order to "load" outer box 2 so as to form a containment 3 comprising outer box 2 as well as one or more, preferably a stack of individual pouches 1a, outer box 2 is completely opened as this is shown in FIG. 5. A stack of pouches 1a is then inserted into box 2 as this is shown in FIG. 6. After having completed the loading, upstanding post 20 provided on the bottom 21 of box 2 extends through oblong holes 11 of pouches 1a.

Once the stack of individual pouches 1a has been inserted (see FIG. 6), lid 25 is pivoted about living hinge 29 and is closed. This is represented in FIG. 7, with closure 26 still being open. In order to allow the lid to be releasably retained in the closed state, resilient cams 251 (see FIG. 5 and FIG. 6) are provided at lid 25 and corresponding grooves (not shown) and 231 are provided in side-walls 22,23 to accommodate resilient cams 251. In addition, a small peg 252 may extend from lid 25 for fitting into a respective hole 202 provided in the upper surface of upstanding post 20, thus aiding in precisely positioning lid 25 relative to the rest of the box as the lid 25 is closed and further ensuring, that no pouch 1a may "escape" between the upper end of upstanding post 20 and lid 25.

In the position shown in FIG. 7, containment 3 which comprises outer box 2 containing the stack of pouches 1a is now ready for use. As can be seen in FIG. 7, both the pouches 1a as well as the outer box 2 at its open 27 end have an undulating shape, however, the undulation of pouches 1a is inverse to the undulation of outer box 2. This serves to expose pouch 1a at its longitudinal end at that side where the upstanding post 20 is arranged in outer box 2, so that grasping an individual pouch 1a at the location where it is exposed facilitates removal of a single individual pouch 1a from outer box 2. Upon grasping the uppermost located pouch 1a and pulling it out of the box, upstanding post 20 causes pouch 1a to rupture along preset rupturing line 12, that is in the direction of the longitudinal extension of pouch 1a. Pouch 1a is thus opened along an essential part of its longitudinal extension thus allowing convenient access to film strip FS contained in the pocket of pouch 1a (similar to FIG. 1). Also, pouch 1a is completely removed from the outer box 2 with no rest of the pouch being retained in outer box 2.

After having removed pouch 1a from outer box 2, outer box 2 can be closed again. This is performed by pivoting closure 26 about living hinge 28 back to the closed position shown in FIG. 4. When outer box 2 is in the closed locked state, resiliently attached cams 260 are snapped into holes 220 and 230, thus retaining closure 26 in its position and preventing unintentional access to the inner space of box 2 where pouches 1a are arranged.

A second embodiment of the box according to the invention and of the containment according to the invention will now be described with reference to FIGS. 8-11. The reference signs used will be generally similar to those of the first embodiment, however, the letter "a" will be added to identify that the respective reference sign belongs to the second embodiment of the containment or the box, respectively. Accordingly, FIG. 8 and FIG. 9 show outer box 2a comprising a bottom 21a, two side walls 22a and 23a, an end wall 24a, a lid 25a and a closure 26a. As can be seen from FIG. 9, closure 26a is a separately manufactured piece that is pivotally attached to the rest of box 2a by means of a small axle 28a and a respective sleeve 261a integrally formed with closure 26a.

Turning back to FIG. 8, box 2a is in the locked state. In order to retain box 2a in the locked state, two cams 260a are resiliently attached to closure 26a. Two holes 250a and 210a are provided in lid 25a and in bottom 21a, respectively (different from the first embodiment, where the cams and holes were attached to form a laterally arranged snap-fit interengagement). An upstanding post 20a having a pointed edge 200a extends from bottom 21a. At the end wall 24a, lid 25a is attached by means of a further living hinge 29a (see FIG. 9).

In order to "load" outer box 2a so as to form a containment 3a comprising outer box 2a containing one or more, preferably a stack of pouches 1a, outer box 2a is completely opened as this is shown in FIG. 9. Ribs 222a and 232a are provided at the side-walls 22a and 23a, respectively, which provide for additional stability of box 2a on one hand and for allowing a smooth and centered insertion of pouches 1a into outer box 2a. A stack of pouches 1a is then inserted into box 2a as this is shown in FIG. 10. After the loading, upstanding post 20a provided on the bottom 21a of box 2a extends through oblong holes 11 of pouches 1a.

Once the stack of pouches 1a has been inserted (see FIG. 10), lid 25a is pivoted about living hinge 29a and is closed. This is represented in FIG. 11, with closure 26 still being open. In order to allow lid 25a to be releasably retained in the closed state, resilient cams 251 (see FIG. 9 and FIG. 10) are provided at lid 25a, and corresponding grooves 221a (not shown) and 231a are provided in side-walls 22a and 23a to accommodate cams 251a. In addition, a small peg 252a extends from lid 25a for fitting into a respective hole 202a provided in the upper surface of upstanding post 20a, thus aiding in precisely positioning lid 25a relative to the rest of the box as lid 25a is closed and further ensuring, that no pouch 1*a* may "escape" between the upper end of upstanding post 20*a* and lid 25*a*. Also, a little termination sleeve 253*a* is integrally formed with lid 25*a* accommodating the upper end of axle 28*a* when closing lid 25*a* so as to avoid, that closure 26*a* may "escape".

In the position shown in FIG. 11, containment 3*a* which comprises outer box 2*a* containing the stack of pouches 1*a* is now ready for use. As can be seen in FIG. 11, both the pouches 1*a* as well as the outer box at its open end have an undulating shape, however, the undulation of pouches 1*a* is inverse to the undulation of outer box 2*a*. This serves to expose pouch 1*a* at its longitudinal end and at that side where the upstanding post 20*a* is arranged in outer box 2*a*, so that grasping pouch 1*a* at the location where it is exposed facilitates removal of pouch 1*a* from outer box 2*a*. As one can easily recognize, it is not mandatory that the undulated shape of outer box 2*a* is inverse to the undulated shape of pouches 1*a*—the intention is merely to expose pouch 1*a* a that side where upstanding post 20*a* is arranged. Upon grasping the uppermost located pouch 1*a* and pulling it out of box 2*a*, upstanding post 20*a* causes pouch 1*a* to rupture along preset rupturing line 12, that is in the direction of the longitudinal extension of pouch 1*a*. Pouch 1*a* is thus opened along an essential part of its longitudinal extension thus allowing convenient access to film strip FS contained in pouch 1*a* (see FIG. 1). Also, pouch 1*a* is completely removed from the outer box 2*a* with no rest of the pouch being retained in outer box 2*a*.

After having removed pouch 1*a* from outer box 2*a*, outer box 2*a* can be closed and locked again. This is performed by pivoting closure 26*a* about the laterally arranged hinge formed by axle 28*a* and sleeve 261*a* back to the locked position shown in FIG. 8. When outer box 2*a* is in the locked state, resiliently attached cams 260*a* are snapped into holes 250*a* and 210*a*, thus retaining closure 26*a* in the locked position and preventing unintentional access to the inner space of box 2*a* where pouches 1*a* are arranged.

A third embodiment of the box according to the invention and of the containment according to the invention will now be described with respect to FIGS. 12-15. The reference signs used will be similar to those of the first embodiment, however, the letter "b" will be added to identify that the respective reference sign belongs to the third embodiment of the containment or the box, respectively. Accordingly, FIG. 12 and FIG. 13 show outer box 2*b* comprising a bottom 21*b*, two side walls 22*b* and 23*b*, an end wall 24*b*, a lid 25*b* and a closure 26*b*. Closure 26*b* is integrally formed with box 2*b* and is hingedly attached to the rest of box 2*b* by a living hinge (not shown, but similar to FIG. 5)

Turning back to FIG. 12, box 2*b* is in the closed state. In order to retain box 2*b* in the closed state, two cams 220*b* and 230*b* are resiliently attached to side-walls 22*b* and 23*b* and corresponding holes 260*b* are provided at closure 26*b*. An upstanding post 20*b* having a pointed edge 200*b* extends from bottom 21*b*. Lid 25*b* is a separately manufactured part which may be attached and detached to and from the rest of box 2*b* by means of resiliently attached cams 251*b* through interengagement with corresponding grooves 221*b* (not shown) and 231*b* provided in side-walls 22*b* and 23*b*, respectively.

In order to "load" outer box 2*b* so as to form a containment 3*b* comprising outer box 2*b* as well as one or more, preferably a stack of pouches 1, outer box 2*b* is completely opened as this is shown in FIG. 12. Ribs 222*b* and 232*b* are provided at the side-walls 22*b* and 23*b*, respectively, which provide for additional stability of box 2*b* on one hand, and on the other hand for allowing a smooth and centered insertion of pouches 1 into outer box 2*b*. A stack of pouches 1 is then inserted into box 2*b* as this is shown in FIG. 14. After the loading, upstanding post 20*b* provided on the bottom 21*b* of box 2*b* extends through oblong holes 11 of pouches 1.

Once the stack of pouches 1 has been inserted (see FIG. 14), lid 25*b* is attached to the rest of the box by means of snap-fitting the cams 251*b* and grooves 221*b* (not shown) and 231*b*. This is represented in FIG. 15, with closure 26*b* still being open.

In the position shown in FIG. 15, containment 3*b* comprising outer box 2*b* as well as the stack of pouches 1 is now ready for use. As can be seen in FIG. 15, outer box 2*b* at its open end has an undulating shape, while the shape of pouch 1 is not undulated. This serves to expose pouch 1*a* at its longitudinal end and at that side where the upstanding post 20*b* is arranged in outer box 2*b*, so that grasping pouch 1 at the location where it is exposed facilitates removal of pouch 1 from outer box 2*b*. Arrow 13 on the upper surface of pouch 1 indicates to the user to pull pouch 1 out of outer box 2*b*. Upon grasping the uppermost located pouch 1 and pulling it out of the box, upstanding post 20*b* causes pouch 1 to rupture along preset rupturing line 12, that is in the direction of the longitudinal extension of pouch 1. Pouch 1 is thus opened along an essential part of its longitudinal extension thus allowing convenient access to film strip FS contained in pouch 1 (see FIG. 1). Also, pouch 1 is completely removed from outer box 2*b* with no rest of the pouch being retained in outer box 2*b*.

After having removed pouch 1 from outer box 2*b*, outer box 2*b* can be closed again. This is performed by pivoting closure 26*b* about the living hinge back to the locked position shown in FIG. 12. When outer box 2*b* is in the locked state, resiliently attached cams 220*b* and 230*b* are snapped into holes 260*b*, thus retaining closure 26*b* in its position and preventing unintentional access to the inner space of box 2*b* where pouches 1 are arranged.

A fourth embodiment of the box according to the invention and of the containment according to the invention is described hereinbelow with respect to FIGS. 16-19. The reference signs used will be similar to those of the first embodiment, however, the letter "c" will be added to identify that the respective reference sign belongs to the fourth embodiment of the containment or the box, respectively. Accordingly, FIG. 16 and FIG. 17 show outer box 2*c* comprising a bottom 21*c*, two side walls 22*c* and 23*c*, an end wall 24*c*, a lid 25*c* and a closure 26*c*. Closure 26*c* is integrally formed with the rest of the box 2*c* and is hingedly attached to the rest of box 2*c* by a living hinge 28*c*.

In FIG. 16 box 2*c* is shown in closed state. In order to retain box 2*c* in the closed state, two cams 220*c* and 230*c* are resiliently attached to side-walls 22*c* and 23*c* and corresponding holes 260*c* are provided at closure 26*c*. Additionally, closure 26*c* has a peg 263*c* (see FIGS. 18 and 19) and lid 25*c* has a through-hole 256*c*. In the closed state cams 220*c* and 230*c* are snapped into the corresponding holes 260*c* and peg 263*c* extends into through-hole 256*c*. For releasing the closure 26*c* to open the box 2*c*, closure 26*c* has two release buttons 262*c*. By means of pushing said release buttons 262*c* and additionally pressing lid 25*c* in a direction towards the inner space of box 2*c*, the cams 220*c* and 230*c* as well as the peg 263*c* are moved out of the corresponding holes 260*c* or through-hole 256*c*, respectively, such that closure 26*c* is unlocked state and is ready to be opened.

To simplify pressing of the lid 25*c* by a user of box 2*c*, lid 25*c* has a finger receiver 254*c* being arranged near through-hole 256*c*, such that the pressure to be applied to remove peg 263*c* out of through-hole 256*c* can be minimized. Further, an edge of the lid 255*c* being arranged adjacent to an edge of the closure when the box is in the closed state, is thicker than the edge of the closure 26*c*, such that it projects above the edge of the closure 26c. This arrangement of the edge of the lid 255c ensures that no gap between the two edges is formed even after the lid has been pressed for a plenty of times.

The described means for locking the closure 26c provide for a safe closing of box 2c and prevent unintentional access to the inner space of box 2c. In particular, box 2c provides a child resistant closure 26c such that any content of the box 2c can not be accessed by children without assistance of adults.

Referring back to FIG. 17, an upstanding post 20c having a pointed edge extends from bottom 21c. Lid 25c is a separately manufactured part which may be attached and detached to and from the rest of box 2c by means of resiliently attached conical pins 258c. The pins 258c are intended to be received by corresponding pin receivers 223c and 233c being arranged at the side-walls 22c and 23c of the rest of the box 2c.

In order to "load" outer box 2c so as to form a containment 3c comprising outer box 2c as well as one or more pouches 1, preferably a stack of pouches 1, box 2c is completely opened with the lid 25c being disassembled as this is shown in FIGS. 17 and 19. The pins 223c and 233c as well as the ribs 242c being arranged at the side-walls 22c and 23c or at the end-wall 24c, respectively, provide for additional stability of box 2c on one hand, and on the other hand they allow a smooth and centered insertion of pouches 1 into box 2c. A stack of pouches 1 is then inserted into box 2c as this is shown in FIG. 19. After loading, upstanding post 20c provided on the bottom 21c of box 2c extends through oblong holes 11 of pouches 1.

Once the stack of pouches 1 has been inserted (see FIG. 19), lid 25c is attached to the rest of the box by means of pins 258c in the corresponding pin receivers 223c and 233c. This is represented in FIG. 18, with closure 26c still being open.

In the position shown in FIG. 18, containment 3c comprising outer box 2c as well as the stack of pouches 1 is ready for use. As can be seen in FIG. 18, outer box 2c at its open end has an undulating shape, while the shape of pouch 1 is not undulated. This serves to expose pouch 1 at its longitudinal end and at that side where the upstanding post 20c is arranged in outer box 2c, so that grasping pouch 1 at the location where it is exposed facilitates removal of pouch 1 from outer box 2c. Arrow 13 on the upper surface of pouch 1 indicates to the user to pull pouch 1 out of outer box 2c (this arrow may not be kept in the final design, isn't it an issue to keep it in there ?). Upon grasping the uppermost located pouch 1 and pulling it out of the box 2c, upstanding post 20c causes pouch 1 to rupture along preset rupturing line 12, that is in the direction of the longitudinal extension of pouch 1 (same as for the arrow above, this rupturing line may not be kept in the final design). Pouch 1 is thus opened along an essential part of its longitudinal extension thus allowing convenient access to film strip FS contained in pouch 1 (see FIG. 1). Also, pouch 1 is completely removed from outer box 2c with no rest of the pouch being retained in box 2c.

After having removed pouch 1 from box 2c, box 2c can be closed again. This is performed by pivoting closure 26c about the living hinge 28c back to the locked position shown in FIG. 16. When outer box 2c is in the locked state, the resiliently attached cams 220c and 230c are snapped into holes 260c and peg 263c extends into through-hole 256c, thus retaining closure 26b in its position.

While various embodiments have been described above with reference to the drawings, it is to be understood that numerous changes and modifications can be made without departing from the spirit and scope of the invention, which is defined by the appended claims.

Further, it is to be understood that the above described box with the preferred locking mechanism can as well be used for other purposes than for being equipped with pouches. It can be arranged in various embodiments not described above, in particular, in embodiments without posts as e.g. embodiments to be loaded with blister packages or chewing gums.

The invention claimed is:

1. A containment comprising an outer box defining an inner space where a stack of individual pouches is arranged, the individual pouches each having a pocket containing a product, each pouch being designed to be individually removed from the stack, the outer box comprising a closure for preventing/allowing access to the individual pouches and further comprising means for interacting with the pouches in a manner such as to allow access to the pocket of an individual pouch upon removing the pouch from the stack, wherein the means for interacting with the pouches, upon removing a pouch from the stack, causes the pouch to open along a part of a longitudinal dimension of the pouch, thereby opening the pocket, and the pouch is completely removed from the outer box with no residual part of the pouch remaining in the outer box.

2. The containment according to claim 1, wherein the outer box comprises a bottom, two side-walls, a lid, and an open end allowing access to the pouches when the closure is open, and wherein the means for interacting with the pouches comprise an upstanding post arranged on the bottom of the outer box in a region close to the open end of the outer box, the upstanding post extending through a hole provided in an end region of each of the pouches.

3. The containment according to claim 2, wherein the upstanding post has a pointed edge facing in the direction of the longitudinal extension of the pouches.

4. The containment according to claim 1, wherein the closure is hingedly attached to the rest of the outer box.

5. The containment according to claim 4, wherein the closure is a piece manufactured separately from the outer box and is pivotally attached to the rest of the outer box by means of a laterally arranged hinge.

6. The containment according to claim 4, wherein the closure is a piece integrally formed with the rest of the outer box and is attached to an edge at the open end of the outer box by a living hinge.

7. The containment according to claim 1 wherein the closure as well as the rest of the outer box both comprise interengaging means allowing to retain the closure in a locked state so as to prevent access to the pouches and to release it for allowing access to the pouches.

8. The containment according to claim 7, wherein the closure as well as the rest of the outer box both comprise a plurality of spatially separated interengaging means being arranged such that the closure is releasable from the locked state only when all of the plurality of interengaging means are operated.

9. The containment according to claim 8, wherein the plurality of interengaging means is arranged such that the closure is releasable from the locked state when all of the plurality of interengaging means are operated simultaneously.

10. The containment according to claim 7, wherein the interengaging means comprise a releasable snap-fit.

11. The containment according to claim 7, wherein the lid as well as the closure both comprise additional interengaging means allowing to retain the closure in the locked state to prevent access and to release it for allowing access to the inner space of the box.

12. The containment according to claim 11, wherein the lid has receiving means for receiving a finger of a user to apply pressure for operating the additional interengaging means for releasing the closure from the lid.

13. The containment according to claim 11, wherein an edge of the lid being arranged adjacent to an edge of the closure when the box is in the locked state projects above the edge of the closure.

14. The containment according to claim 2, wherein the lid of the outer box is hingedly attached to the rest of the outer box.

15. The containment according to claim 14, wherein the lid is integrally formed with the rest of the outer box and is attached to an edge of the end wall via a living hinge.

16. The containment according to claim 2, wherein both the outer box at its open end as well as the pouches at their respective ends are shaped such, that the pouches are exposed at that side where the upstanding post is arranged.

17. The containment according to claim 1, wherein the pouch has a marking on its upper side indicating the direction the pouch is to be pulled out of the outer box.

* * * * *

UNITED STATES PATENT AND TRADEMARK OFFICE
CERTIFICATE OF CORRECTION

PATENT NO. : 7,661,534 B2 Page 1 of 1
APPLICATION NO. : 11/455033
DATED : February 16, 2010
INVENTOR(S) : Saclier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 418 days.

Signed and Sealed this

Thirtieth Day of November, 2010

David J. Kappos
*Director of the United States Patent and Trademark Office*